(12) United States Patent
Froehlich et al.

(10) Patent No.: US 9,650,629 B2
(45) Date of Patent: May 16, 2017

(54) CLONAL PRE-AMPLIFICATION IN EMULSION

(75) Inventors: Thomas Froehlich, Bichl (DE); Tobias Heckel, Basel (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 61 days.

(21) Appl. No.: 13/169,110

(22) Filed: Jun. 27, 2011

(65) Prior Publication Data
US 2012/0010086 A1 Jan. 12, 2012

(30) Foreign Application Priority Data
Jul. 7, 2010 (EP) ..................................... 10168732

(51) Int. Cl.
*C12N 15/10* (2006.01)
(52) U.S. Cl.
CPC ......... *C12N 15/1075* (2013.01); *C12N 15/10* (2013.01); *C12N 15/1096* (2013.01)
(58) Field of Classification Search
None
See application file for complete search history.

(56) References Cited

U.S. PATENT DOCUMENTS

| | | | |
|---|---|---|---|
| 5,118,801 A | 6/1992 | Lizardi et al. | |
| 5,210,015 A | 5/1993 | Gelfand et al. | |
| 5,487,972 A | 1/1996 | Gelfand et al. | |
| 5,538,848 A | 7/1996 | Livak et al. | |
| 5,804,375 A | 9/1998 | Gelfand et al. | |
| 6,114,149 A * | 9/2000 | Fry et al. ...................... | 435/91.2 |
| 6,174,670 B1 | 1/2001 | Wittwer et al. | |
| 7,575,865 B2 | 8/2009 | Leamon et al. | |
| 2005/0130173 A1* | 6/2005 | Leamon et al. ................... | 435/6 |
| 2012/0010091 A1* | 1/2012 | Linnarson ......................... | 506/7 |

FOREIGN PATENT DOCUMENTS

| | | | | |
|---|---|---|---|---|
| EP | 1482036 B1 | 10/2007 | | |
| EP | 2224014 A1 | 9/2010 | | |
| SE | WO 2010117620 A2 * | 10/2010 | ......... | C12N 15/1065 |
| WO | 2005/003375 A3 | 1/2005 | | |
| WO | 2005/073410 A3 | 8/2005 | | |
| WO | 2008/073378 A3 | 6/2008 | | |
| WO | 2009/148560 A8 | 12/2009 | | |

OTHER PUBLICATIONS

Sauer et al. Nucleic Acids Research (2000) 28(5): e13.*
Ge et al. Clinica Chimica Acta (2006) 369: 82-88.*
Kurimoto et al. Nucleic Acids Research (2006) 34(5): e42.*
Extended European Search Report issued Mar. 22, 2011 in European Application No. 10168732.5.
Ayala, Francisco J., "Darwin's greatest discovery: Design without designer," Proceedings of the National Academy of Sciences USA, May 15, 2007, pp. 8567-8573, vol. 104, Supplement 1.
Brown, Patrick O. and Botstein, David, "Exploring the new world of the genome with DNA microarrays," Nature Genetics Supplement, Jan. 1999, pp. 33-37, vol. 21.
Chambers, Ian et al., "Nanog safeguards pluripotency and mediates germline development," Nature, Dec. 20/27, 2007, pp. 1230-1234, vol. 450.
Dean, Frank B. et al., "Comprehensive human genome amplification using multiple displacement amplification," Proceedings of the National Academy of Sciences USA, Apr. 16, 2002, pp. 5261-5266, vol. 99, No. 8.
Deangelis, Margaret M. et al., "Solid-phase reversible immobilization for the isolation of PCR products," Nucleic Acids Research, 1995, pp. 4742-4743, vol. 23, No. 22.
Diercks, Alan et al., "Resolving Cell Population Heterogeneity: Real-Time PCR for Simultaneous Multiplexed Gene Detection in Multiple Single-Cell Samples," PLoS One, Jul. 2009, e6326 (9 pages), vol. 4, Issue 7.
Esteban, José A. et al., "Fidelity of ø29 DNA Polymerase Comparison Between Protein-Primed Initiation and DNA Polymerization," The Journal of Biological Chemistry, Feb. 5, 1993, pp. 2719-2726, vol. 268, No. 4.
Guttmacher, Alan E. and Collins, Francis S., "Genomic Medicine—A Primer," The New England Journal of Medicine, Nov. 7, 2002, pp. 1512-1520, vol. 347, No. 19.
Hori, Machiko et al., "Uniform amplification of multiple DNAs by emulsion PCR," Biochemical and Biophysical Research Communications, 2007, pp. 323-328, vol. 352.
Kamme, Fredrik et al., "Single-Cell Microarray Analysis in Hippocampus CA1: Demonstration and Validation of Cellular Heterogeneity," The Journal of Neuroscience, May 1, 2003, pp. 3607-3615, vol. 23, No. 9.
Kamme, Fredrik et al., "Single-Cell Laser-Capture Microdissection and RNA Amplification," from Methods in Molecular Medicine, vol. 99: Pain Research: Methods and Protocols, 2004, pp. 215-223, Z. D. Luo, Editor, Humana Press Inc., Totowa, NJ.
Klein, Christoph A. et al., "Comparative genomic hybridization, loss of heterozygosity, and DNA sequence analysis of single cells," Proceedings of the National Academy of Sciences USA, Apr. 1999, pp. 4494-4499, vol. 96.
Kurn, Nurith et al., "Novel Isothermal, Linear Nucleic Acid Amplification Systems for Highly Multiplexed Applications," Clinical Chemistry, 2005, pp. 1973-1981, vol. 51, No. 10.
Lasken, Roger S. and Egholm, Michael, "Whole genome amplification: abundant supplies of DNA from precious samples or clinical specimens," Trends in Biotechnology, Dec. 2003, pp. 531-535, vol. 21, No. 12.
Livak, Kenneth J. and Schmittgen, Thomas D., "Analysis of Relative Gene Expression Data Using Real-Time Quantitative PCR and the 2-ΔΔCT Method," Methods, 2001, pp. 402-408, vol. 25.

(Continued)

*Primary Examiner* — Angela M Bertagna
(74) *Attorney, Agent, or Firm* — McDonnell Boehnen Hulbert & Berghoff LLP

(57) ABSTRACT

Disclosed is a process for clonal pre-amplification of a nucleic acid involving the steps of (i) providing a plurality of different nucleic acid molecules (b) attaching adaptor sequences to the 3' ends and 5' ends of the nucleic acid molecules (c) preparing a water in oil emulsion wherein the majority of water droplets comprises one or none member of the plurality of different nucleic acid molecules (d) clonally amplifying the plurality of different nucleic acid molecules. In particular, the different nucleic acid molecules are mRNA molecules.

18 Claims, 3 Drawing Sheets

(56) References Cited

OTHER PUBLICATIONS

Lundberg, Kelly S. et al., "High-fidelity amplification using a thermostable DNA polymerase isolated from *Pyrococcus furiosus*," Gene, 1991, pp. 1-6, vol. 108.
Margulies, Marcel et al., "Genome sequencing in microfabricated high-density picolitre reactors," Nature, Sep. 15, 2005, pp. 376-380, vol. 437; with Errata & Corrigenda, May 4, 2006, p. 120, vol. 441.
McCarty, Maclyn, "Discovering genes are made of DNA," Nature, Jan. 23, 2003, p. 406, vol. 421.
Meyerhans, Andreas et al., "DNA recombination during PCR," Nucleic Acids Research, 1990, pp. 1687-1691, vol. 18, No. 7.
Mullis, K. et al., "Specific Enzymatic Amplification of DNA In Vitro: The Polymerase Chain Reaction," Cold Spring Harbor Symposia on Quantitative Biology, 1986, pp. 263-273, vol. LI.
Nakano, Michihiko et al., "Single-molecule PCR using water-in-oil emulsion," Journal of Biotechnology, 2003, pp. 117-124, vol. 102.
Nakano, Michihiko et al., "Single-Molecule Reverse Transcription Polymerase Chain Reaction Using Water-in-Oil Emulsion," Journal of Bioscience and Bioengineering, 2005, pp. 293-295, vol. 99, No. 3.
Peano, Clelia et al., "Transciptome amplification methods in gene expression profiling," Expert Review of Molecular Diagnostics, 2006, pp. 465-480, vol. 6, No. 3.
Saitou, Mitinori et al., "A molecular programme for the specification of germ cell fate in mice," Nature, Jul. 18, 2002, pp. 293-300, vol. 418.
Schmittgen, Thomas D. and Livak, Kenneth J., "Analyzing real-time PCR data by the comparative CT method," Nature Protocols, 2008, pp. 1101-1108, vol. 3, No. 6.
Shendure, Jay and Ji, Hanlee, "Next-generation DNA sequencing," Nature Biotechnology, Oct. 2008, pp. 1135-1145, vol. 26, No. 10.
Stoecklein, Nikolas H. et al., "Direct Genetic Analysis of Single Disseminated Cancer Cells for Prediction of Outcome and Therapy Selection in Esophageal Cancer," Cancer Cell, May 2008, pp. 441-453, vol. 13.
Tang, Fuchou et al., "mRNA-Seq whole-transcriptome analysis of a single cell," Nature Methods, May 2009, pp. 377-382, vol. 6, No. 5.
Toyooka, Yayoi et al., "Identification and characterization of subpopulations in undifferentiated ES cell culture," Development, 2008, pp. 909-918, vol. 135.
Van Gelder, Russell N. et al., "Amplified RNA synthesized from limited quantities of heterogeneous cDNA," Proceedings of the National Academy of Sciences USA, Mar. 1990, pp. 1663-1667, vol. 87.
Vogelstein, Bert and Gillespie, David, "Preparative and analytical purification of DNA from agarose," Proceedings of the National Academy of Sciences USA, Feb. 1979, pp. 615-619, vol. 76, No. 2.
Walker, G. Terrance et al., "Isothermal in vitro amplification of DNA by a restriction enzyme/DNA polymerase system," Proceedings of the National Academy of Sciences USA, Jan. 1992, pp. 392-396, vol. 89.
Wang, Ena, "RNA Amplification for successful gene profiling analysis," Journal of Translational Medicine, Jul. 25, 2005, 11 pages, vol. 3, No. 28.
Williams, Richard et al., "Amplification of complex gene libraries by emulsion PCR," Nature Methods, Jul. 2006, pp. 545-550, vol. 3, No. 7.
"Genome Sequencer System, Roche Application Note No. 8," Oct. 2007, Retrieved from the Internet http://genoseq.ucla.edu/images/d/db/RNA_virus_pdf [retrieved Mar. 8, 2011].
Xu, Feng et al., "Construction of cDNA library of Magnaporthe grisea with magneticbead," Acta Microbiologica Sinica, 2008, pp. 806-810, vol. 48, No. 6, English Abstract.
Schramm, Guido et al., "A simple and reliable 5'-RACE approach," Nucleic Acids Research, 2000, e96, 4 pages, vol. 28, No. 22.
Zhu, Y. Y. et al., "Reverse Transcriptase Template Switching: A SMART(TM) Approach for Full-Length cDNA Library Construction," BioTechniques, 2001, pp. 892-897, vol. 30, No. 4.
Invitrogen (TM) Life Technologies Instrustion Manual, 5' RACE System for Rapid Amplification of cDNA Ends, Version 2.0, Catalog No. 18374-058, 2004, 1-48, Version E.
Anonymous, "5'/3' RACE kit, 2nd Generation, Version 9.0", ROCHE Cat. No. 03 353 621 001 instruction manual, Nov. 2007. Retrieved from the Internet at URL https://pim-eservices.roche.com/LifeScience/Document/820df4f0-c0ed-e311-98a1-00215a9bOba8—last accessed Dec. 30, 2016.

\* cited by examiner

CLONAL PRE-AMPLIFICATION IN EMULSION

RELATED APPLICATIONS

This application claims priority to European application EP 10168732.5 filed Jul. 7, 2010.

FIELD

The invention relates to the field of nucleic acid amplification. More particularly, the invention provides methods, compositions and kits for amplifying (i.e., making multiple copies of) target nucleic acid sequences which employs compartmentalization such that each compartment contains a single, or at most a few, target nucleic acid molecules.

BACKGROUND

Since the discovery that genes, the hereditary material, are made up of nucleic acids (McCarthy, M., Nature 421 (2003) 406) and that genetic alterations are a molecular basis of disease (Guttmacher, A. E. and Collins, F. S., N. Engl. J. Med. 347 (2002) 1512-1520) and evolution (Ayala, F. J., Proc. Natl. Acad. Sci. USA 104, Suppl. 1 (2007) 8567-8573) nucleic acids became prominent target molecules of investigation. The most powerful and versatile methods for the investigation of nucleic acids on the genomic scale are microarrays (Brown, P. O. and Botstein, D., Nat. Genet. 21 (1999) 33-37) and high-throughput sequencer of the second or third generation (Shendure, J. and Ji, H., Nat. Biotechnol. 26 (2008) 1135-1145). These techniques usually need microgram amounts of nucleic acids for analysis, which corresponds to hundreds of thousands of mammalian cells (Peano, C. et al., Expert Rev. Mol. Diagn. 6 (2006) 465-480; Tang, F. et al., Nat. Methods 6 (2009) 377-382).

However, under many important conditions, it is practically impossible to get such large amounts of material. For example, techniques used to isolate human tissues, such as biopsy, fine-needle aspiration, cytolavage and laser capture microdissection, often achieve yields of extracted nucleic acids in the nanogram range (Kamme, F. et al., Methods Mol. Med. 99 (2004) 215-223). Other examples are coming form the fields of development studies, embryo cells, neuron, immune cell, cancer cell or stem cell research (Saitou, M. et al., Nature 418 (2002) 293-300; Chambers, I. et al., Nature 450 (2007) 1230-1234; Toyooka, Y. et al., Development 135 (2008) 909-918; Kamme, F. et al., J. Neurosci. 23 (2003) 3607-3615; Stoecklein, N. H. et al., Cancer Cell 13 (2008) 441-453; Diercks, A. et al., PLoS One 4 (2009) e6326). In fact, during mouse early development, when the founder population of germline, primordial germ cells have just emerged, there are only around 30 primordial germ cells in the embryo (Saitou, M. et al., Nature 418 (2002) 293-300). Even for in vitro-cultured stem cells, for which the number of cells would appear to be unlimited, there are serious limitations due to stem cell heterogeneity. For example, mouse embryonic stem cells, probably the most thoroughly analyzed type of stem cells, contain multiple subpopulations with strong differences in both gene expression and physiological function, which in turn promotes the need of genomic analysis on the level of subpopulations or even single cells (Chambers, I. et al., Nature 450 (2007) 1230-1234; Toyooka, Y. et al., Development 135 (2008) 909-918).

Therefore, in order to overcome the limitations of array and high-throughput sequencing technologies and to permit multiple analyses of even a single cell, the development of methods is needed to amplify few amounts of nucleic acid, without significantly distorting the information content of the sample. In this respect, many protocols for nucleic acid amplification of the whole genome as well as of the whole transcriptome have been developed in the last 20 years (Peano, C. et al., Expert Rev. Mol. Diagn. 6 (2006) 465-480; Lasken, R. S. and Egholm, M., Trends Biotechnol. 21 (2003) 531-535). Most of these methods are based upon in vitro transcription reaction, upon isothermal amplification and upon PCR (polymerase chain reaction).

The in vitro transcription method developed by Van Gelder and Eberwine (Van Gelder, R. N. et al., Proc. Natl. Acad. Sci. USA 87 (1990) 1663-1667) enables the linear amplification of RNA. The original method and their technical revisions are based on double stranded cDNA synthesis followed by RNA synthesis. The error rate of in vitro transcription is relatively low, not due the error rate of RNA polymerases (one mismatch for every 10 000 bases of synthesis), but because the input double stranded DNA templates are the only source of template for the complete amplification and, therefore, any errors created on the newly synthesized RNA will not be carried or amplified in the following reactions (Wang, E., J. Transl. Med. 3 (2005) 1-11). In vitro transcription however is burdensome, restricted to RNA samples, generates less stable RNA amplificates and it is time consuming. Furthermore the method is prone to produce a 3' bias introduced by the use of promoter-modified oligo(dT) primer and especially when two rounds of amplification are employed, because the second-round RNA population will be smaller leading to a loss of information in the 5' end of the transcript (Peano, C. et al., Expert Rev. Mol. Diagn. 6 (2006) 465-480; Wang, E., J. Transl. Med. 3 (2005) 1-11).

Most of the isothermal amplification methods are based upon the strand-displacement amplification approach, which relies on DNA polymerases with strong strand displacement activity, such as for example exo-Klenow, Bca, Bst or phi29 DNA polymerases (Dean, F. B. et al., Proc. Natl. Acad. Sci. USA 99 (2002) 5261-5266; Walker, G. T. et al., Proc. Natl. Acad. Sci. USA 89 (1992) 392-396; Kurn, N. et al., Clin. Chem. 51 (2005) 1973-1981). Priming sites for these polymerases are initiated by nick generating restriction enzymes or by random oligonucleotide primers. The unique properties of this reaction allow repeated DNA synthesis over the same template at 30° C., with each new copy displacing previously made copies. Therefore sophisticated instrumentation, like a thermocycler, is not necessary. Furthermore, especially the phi29 DNA polymerase exhibits a robust ability to replicate through difficult sequence as well as an extensive processivity by 10-100 kb at relatively low error rates (1 error every $10^6$-$10^7$ bases) (Dean, F. B. et al., Proc. Natl. Acad. Sci. USA 99 (2002) 5261-5266; Esteban, J. A. et al., J. Biol. Chem. 268 (1993) 2719-2726). However the previously described isothermal amplification methods have drawbacks. Strand-displacement amplification methods such as by Walker, G. T. et al. (Proc. Natl. Acad. Sci. USA 89 (1992) 392-396) require the presence of sites for defined restriction enzymes, which limits its applicability. Randomly primed strand-displacement amplification methods such as by Dean or Kurn et al. (Dean, F. B. et al., Proc. Natl. Acad. Sci. USA 99 (2002) 5261-5266; Kurn, N. et al., Clin. Chem. 51 (2005) 1973-1981) are challenged if they yield products that are non-biased and if they are an accurate and even replication of the original sequence.

PCR mediated exponential amplification developed by Mullis (Mullis K. et al., Cold Spring Harb. Symp. Quant.

Biol. 51 Pt. 1 (1986) 263-273) offers many advantages, such as high amplification yields that suggest the possibility of greatly reducing the amount of input material, together with fast and easy protocols that can drastically reduce the costs of analyses, thus enabling more complex experimental designs. Moreover, double-stranded PCR products are particularly stable. In addition to conventional PCR amplification techniques, methods for performing PCR in emulsion droplets are known in the art (EP 1 482 036; Williams, R. et al., Nat. Methods 3 (2006) 545-550).

However the PCR technology suffers from several drawbacks. First, PCR amplifies small regions of a few hundred nucleotides most efficiently, while, when larger regions are targeted, there is a decrease in the level of amplification. In this way, shorter fragments tend to be amplified in preference to larger ones. Second, amplification of genomic libraries, cDNA libraries and other complex mixtures of genes by PCR suffers from artifactual fragments that are generated by recombination between homologous regions of DNA. Recombination in this case occurs when a primer is partially extended on one template during one cycle of PCR and further extended on another template during a later cycle. Thus, chimeric molecules are generated, the short ones of which are then preferentially amplified (Williams, R. et al., Nat. Methods 3 (2006) 545-550; Meyerhans, A. et al., Nucleic Acids Res. 18 (1990) 1687-1691). Third, supplementary problems in the quality of the amplified nucleic acid sequences originated from the use of *Thermus aquaticus* (Taq) DNA polymerase, which is characterized by a relatively low fidelity. The Taq polymerase error rate (at best, one mismatch for every 50 000 bases of synthesis) results in the incorporation of several erroneous bases in most of the PCR-amplified DNAs (Lundberg, K. S. et al., Gene 108 (1991) 1-6). These misincorporations are propagated through subsequent cycles of the amplification. Fourth, another question concerns the loss of the proportionality of the amplification process. The exponential PCR reaction reaches saturation when excess input template quantities are used, thus favoring the amplification of high abundant over low abundant transcripts. Furthermore the DNA polymerase has low efficiency in the amplification of GC rich sequences as apposed to AT rich sequences (Wang, E., J. Transl. Med. 3 (2005) 28). The different amplification efficiencies can potentially result in several thousand-fold differential representation of DNAs in the DNAs population after as few as 30 cycles of amplification.

In summary the general properties and disadvantages of the current protocols for nucleic acid amplification show that there is a need for improved nucleic acid amplification methods. In particular, there is a requirement for unbiased pre-amplification when material from only a single or only a few cells is available. In this context, the present invention provided herein fulfills this need, overcomes several drawbacks and provides additional benefits.

SUMMARY

In a first aspect, the present invention provides a process for clonal pre-amplification of a nucleic acid comprising the steps of
  a) providing a plurality of different nucleic acid molecules
  b) attaching adaptor sequences to the 3' ends and 5' ends of said nucleic acid molecules
  c) preparing a water in oil emulsion characterized in that the majority of water droplets comprises one or none member of said plurality of different nucleic acid molecules
  d) clonally amplifying said plurality of different nucleic acid molecules In a major embodiment, clonal amplification during step d) is performed in aqueous droplets within a water in oil emulsion.

Preferably, said different nucleic acid molecules are single stranded molecules, preferably RNA molecules more preferably polyadenylated RNA molecules and most preferably mRNA molecules.

In case of RNA molecules, the inventive process may comprise the following steps within step b):
  b1) hybridizing a first single stranded adaptor nucleic acid molecule to said plurality of different nucleic acid molecules, said adapter molecule comprising
    a 5' terminal part representing a primer binding site, and
    a 3' terminal part which is either an oligo dT sequence of at least 5 nucleotides in length, an essentially randomized sequence of at least 5 nucleotides in length or a gene family specific sequence.
  b2) performing a first strand cDNA synthesis in the presence a RNA dependent DNA polymerase and a dNTP mixture in order to generate a pool of single stranded cDNAs
  b3) attaching a second single stranded adaptor molecule to said pool of single stranded cDNAs.

Further in case of RNA molecules, the inventive process may also specifically comprise the following steps:
  b3i) performing a terminal transferase reaction in the presence identical dNTPs in order to create a homopolymer overhang, and
  b3ii) hybridizing a second single stranded adaptor molecule to said pool of single stranded cDNAs, said second single stranded adapter molecule comprising
    a 5' terminal part representing a primer binding site which is either identical or different to the 5' terminal part of said first single stranded adaptor molecule and
    a 3' terminal part of homopolymeric nucleotide residues, which is complementary to said homopolymer overhang created in step b3i).

Preferably, said plurality of different nucleic acid molecules are mRNA molecules. Also preferably, the 3' terminal part of said first single stranded adaptor molecule comprises an oligo dT sequence or a completely randomized sequence, both of at least 5 nucleotides in length. Alternatively, said 3' terminal part comprises a gene or gene family specific sequence.

Subsequent to the inventive process and its modifications described above, the emulsion may be broken up in order to generate the possibility of performing further analytical experiments. For example, the clonally amplified plurality of different nucleic acid molecules may be sequenced. Alternatively, the clonally amplified plurality of different nucleic acid molecules may be subjected to qualitative or quantitative real time PCR reaction experiments using parameter specific amplification primers. Also subsequently gene expression analysis may be performed by means of using microarrays.

The inventive method is especially useful in order to analyze nucleic acids derived from only a small number of cells. In particular when said plurality of different nucleic acid molecules is derived from less than 100 cells, less than 10 cells and even only 1 cell.

In another aspect, the present invention is directed to kits useful for performing the inventive methods as disclosed above.

Such kits will comprise
a first single stranded adaptor nucleic acid molecule comprising
a 5' terminal part representing a primer binding site, and
a 3' terminal part which is either an oligo dT sequence of at least 5 nucleotides in length, or an essentially randomized sequence,
a second single stranded adaptor molecule to said pool of single stranded cDNAs, said second single stranded adapter molecule comprising
a 5' terminal part representing a primer binding site which is either identical or different to the 5' terminal part of said first single stranded adaptor molecule, and
a 3' terminal part of homopolymeric nucleotide residues, and
an RNA dependent DNA polymerase comprising reverse transcriptase activity

DETAILED DESCRIPTION

The present invention provides methods, compositions and kits for amplifying (i.e., making multiple copies of) target nucleic acid sequences.

This technology has wide applicability since nucleic acid analysis is useful for detection and identification of pathogens, detection of gene alteration leading to defined phenotypes, diagnosis of genetic diseases or the susceptibility to a disease, assessment of gene expression in development, disease and in response to defined stimuli, as well as the various genome analysis projects.

Figure 1:
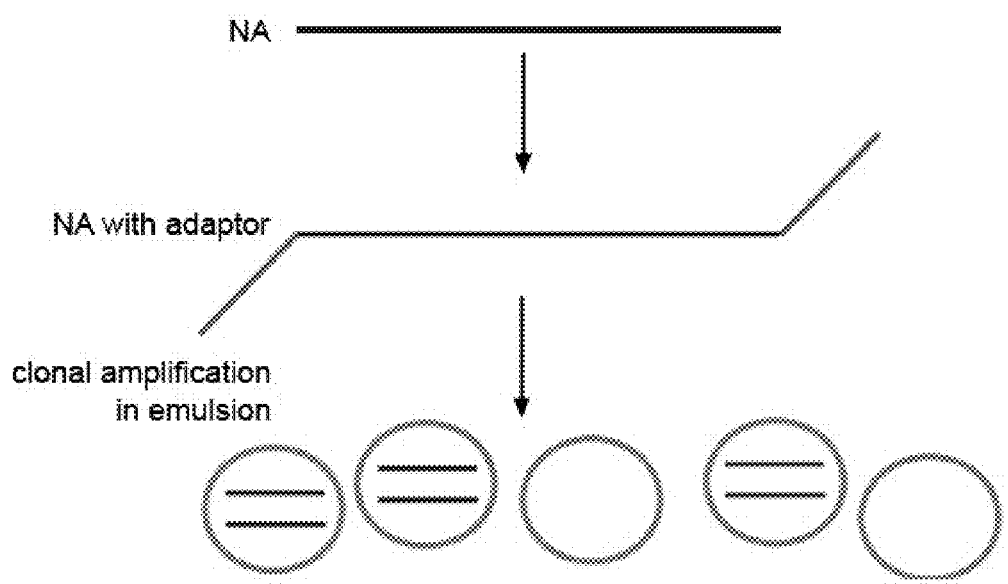
FIG. 1: Schematic drawing of a the general concept for Whole Nucleic Acid amplification in emulsion.

The key concept of the invention is the combination of NA library preparation protocols with the amplification of those libraries in a way that single, or at most a few, target nucleic acid molecules are compartmentalized. Compartmentalization is performed in aqueous droplets of a water-in-oil emulsion. Thereby the template nucleic acid molecules are segregated in the minute aqueous droplets of the emulsion and amplified by PCR in isolation. Due to the small volume of the droplets the concentration of the initial template is risen, which significantly affects the efficiency of amplification, permitting amplification of even a single molecule (Nakano, M. et al., J. Biosci. Bioeng. 99 (2005) 293-295). A schematic drawing is shown in FIG. 1.

Figure 2:
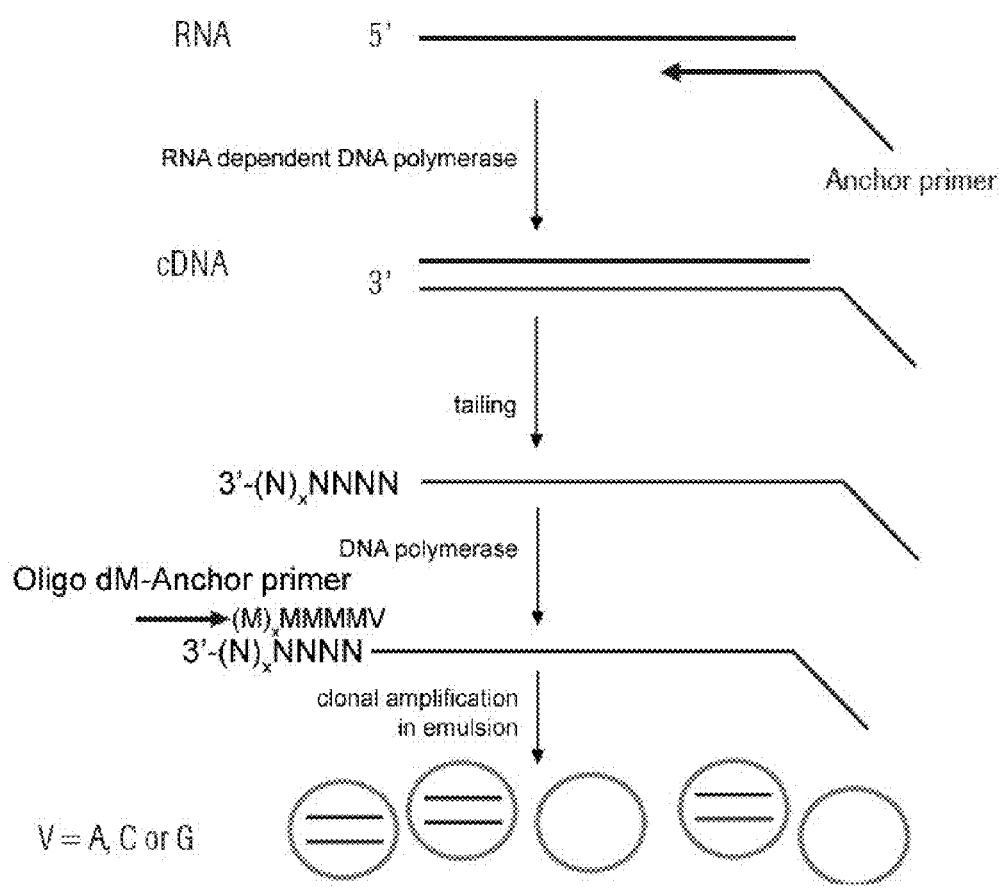
FIG. 2: Schematic drawing of a general concept for whole transcriptome amplification.

A schematic drawing of said key concept when applied to the amplification of whole transcriptome RNA is shown in FIG. 2 Initially, the RNA transcriptome is converted to a cDNA library using a RNA dependent DNA polymerase with reverse transcriptase activity in the presence of anchor-primers consisting of a specific 3' end and a universal 5' end. Second strand cDNA synthesis will be possible after poly(N) tailing using terminal transferase activity creating a cDNA library of fragments with universal end sequences. These fragments are then amplified in emulsion using primers specific for the universal ends.

Figure 3:
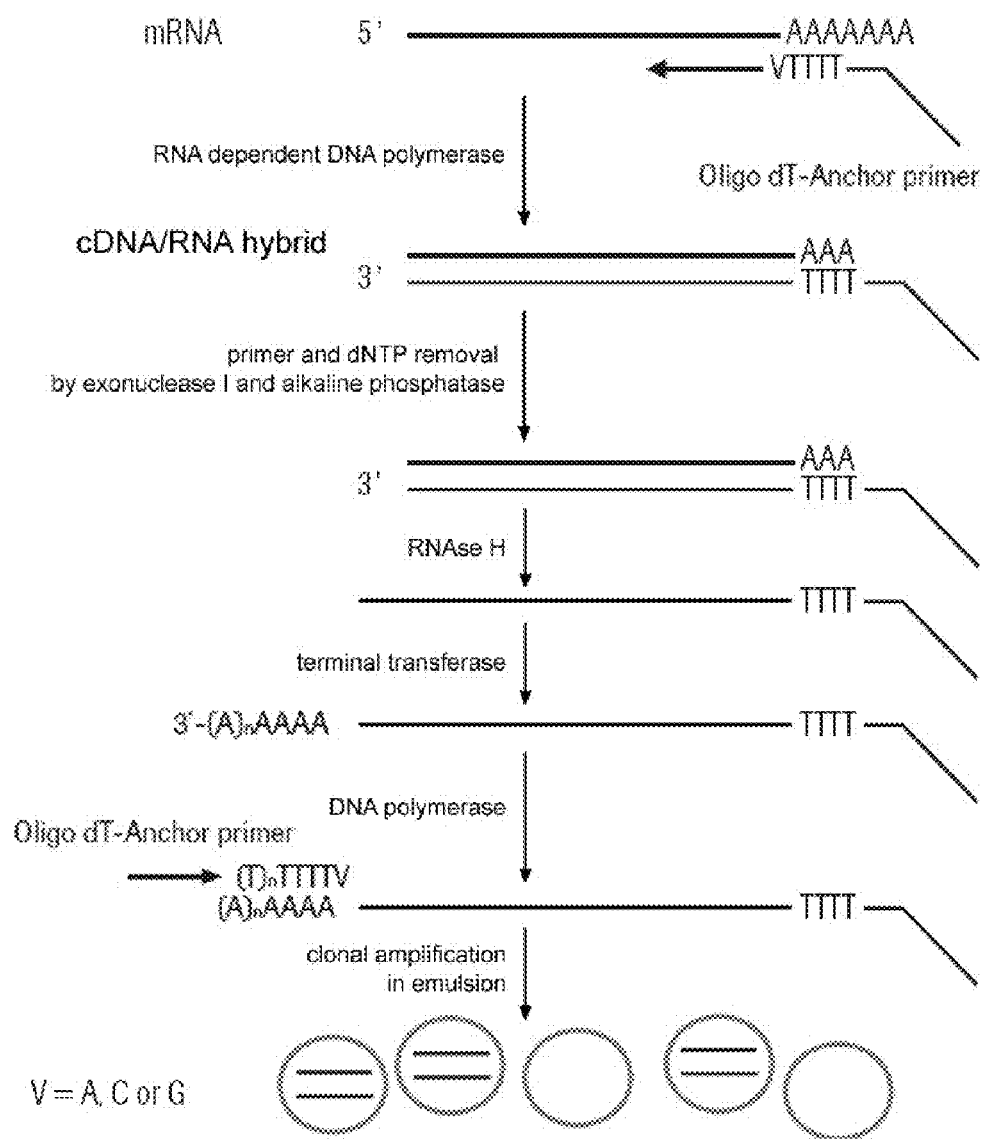
FIG. 3: Schematic drawing of a an example for a process for whole transcriptome amplification

An more detailed example is provided in FIG. 3. Initially, the RNA transcriptome is converted to a cDNA library using a reverse transcriptase in the presence of oligo-(dT)-anchor-primers consisting of a specific 3' end and a universal 5' end. Second strand cDNA synthesis will be possible after removal of unreacted oligo-(dT)-anchor-primers and dNTPs using exonuclease I and alkaline phosphatase treatment. Poly(A) tailing using terminal transferase creates a cDNA library of fragments with universal end sequences on both 5' and 3' ends. These fragments are then amplified in emulsion using primers specific for the universal ends.

A first aspect of the present invention can be defined as a method for clonal pre-amplification of a nucleic acid which comprises the following four steps:
a) providing a plurality of different nucleic acid molecules
b) attaching adaptor sequences to the 3' ends and 5' ends of said nucleic acid molecules
c) preparing a water in oil emulsion characterized in that the majority of water droplets comprises one or none member of said plurality of different nucleic acid molecules'
d) clonally amplifying said plurality of different nucleic acid molecules Step a): Providing a Plurality of Different Nucleic Acid Molecules In principle, the new method is applicable for any kind of nucleic acid such as double stranded DNA, single stranded DNA and in particular any kind of (single stranded) RNA such as ribosomal RNA, t-RNA, snRNA, hnRNA or the like. In particular, the new method is highly advantageous for the clonal preamplification of polyadenylated RNA molecules such as mRNA molecules. Thus, in other words, the present invention provides a new method for unbiased preamplification of a whole transcriptome originating from only a few cells, thereby allowing unbiased gene expression analysis.

The step of providing a plurality of different nucleic acid molecules may comprise any method known in the art which provides a purified DNA or RNA or mRNA sample or cDNA sample and the like. The step may further comprise any known method of nucleic acid fragmentation such as enzymatic digestion, mechanical shearing, sonication, nebulization and the like.

Step b): Attaching Adaptor Sequences to the 3' Ends and 5' Ends of Said Nucleic Acid Molecules In the context of the present invention the term "primer binding site" is frequently used. In this context the term shall be understood as a sequence which is identical to the sequence of a primer which will be used in a subsequent step using a respective primer which is being elongated by a polymerase catalyzed primer extension reaction such as the Polymerase chain reaction.

If the plurality of different nucleic acid molecules that shall be clonally amplified is DNA, then double stranded adaptors are ligated to the ends of each DNA fragment. The adaptor sequences will then serve as universal primer binding sides during the clonal amplification in step d).

The double stranded DNA fragments may be provided in blunt ended form, which may be achieved by methods that are well known in the art. Alternatively, the double stranded fragments may comprise identical single stranded 3' or 5' overhangs, that may be generated upon respective restriction enzyme digest of genomic DNA.

In a preferred specific embodiment, genomic DNA is fragmented by restriction endonuclease treatment. Such a restriction endonuclease could for example be MseI (T|TAA), which produces fragments in the range of 100-1500 bp (Klein, C. A. et al., Proc. Natl. Acad. Sci. USA 96 (1999) 4494-4499). Then Alkaline Phosphatase treatment of DNA fragments is used to prevent their re-ligation. Adaptor oligonucleotides are ligated to the genomic DNA fragments using T4-DNA-Ligase. The adaptor oligonucleotides are of two kinds. One contains a generic sequence with a 5' Phosphate modification. The other one contains a 3' modification to prevent adaptor self-ligation. Such a modification could be either an omitted 3' OH-group or a 3' NH-group or a 3'C7-aminomodifer. Optionally the adaptor could be a chimeric 5'-DNA-3'RNA-oligonucleotide; in this case a RNAse H treatment would destroy such adaptors and eliminate any interference with subsequent PCR amplifications.

Dependent on the type of nucleic acid that shall be clonally amplified, the step of attaching adequate adaptor sequences requires multiple enzymatic treatment steps.

In case of mRNA molecules, the inventive process may comprise the following steps within step b):

b1) hybridizing a first single stranded adaptor nucleic acid molecule to said plurality of different nucleic acid molecules, said adapter molecule comprising
a 5' terminal part representing a primer binding site, and
a 3' terminal part which is either an oligo dT sequence of at least 5 nucleotides in length, an essentially randomized sequence of at least 5 nucleotides in length or a gene family specific sequence.
b2) performing a first strand cDNA synthesis in the presence an RNA dependent DNA polymerase and a dNTP mixture in order to generate a pool of single stranded cDNAs
b3) attaching a second single stranded adaptor molecule to said pool of single stranded cDNAs.

The RNA dependent DNA polymerase may be any polymerase comprising reverse transcriptase activity such as TRANSCRIPTOR (Roche Applied Science Cat. No: 04 379 012 001), AMV reverse transcriptase, M-MuLV reverse transcriptase or a thermostable DNA polymerase with reverse transcriptase activity.

In a preferred embodiment, step b) comprises the following steps:

b1) hybridizing a first single stranded adaptor nucleic acid molecule to said plurality of different nucleic acid molecules, said adapter molecule comprising
a 5' terminal part representing a primer binding site, and
a 3' terminal part which is either an oligo dT sequence of at least 5 nucleotides in length, or an essentially randomized sequence, or a gene family specific sequence.
b2) performing a first strand cDNA synthesis to generate a pool of single stranded cDNAs
b3i) performing a terminal transferase reaction in the presence identical dNTPs in order to create a homopolymer overhang,
b3ii) hybridizing a second single stranded adaptor molecule to said pool of single stranded cDNAs, said second single stranded adapter molecule comprising
a 5' terminal part representing a primer binding site which is either identical or different to the 5' terminal part of said first single stranded adaptor molecule, and
a 3' terminal part of homopolymeric nucleotide residues, which is complementary to said homopolymer overhang created in step b3i).

Said first single stranded adaptor molecule of b1) is designed in such a way that it essentially serves two functions. The 5' terminal primer binding side is introduced in order to enable an amplification of all cDNA molecules during step d) later in the process. The 3' terminal part is designed in such a way that said adaptor molecule is capable of binding and priming reverse transcription of all RNA molecules of interest. For example, in case the complete population of polyadenylated mRNA molecules shall be pre-amplified in full length, the 3' terminal part will comprise a complementary oligo-dT sequence of at least 5 nucleotides or preferably at least 15 but not more than 50 nucleotides in length. Preferably, such primers are designed as anchor-primers. Such an Oligo(dT)-anchor primer is a mixture of oligonucleotides carrying at least one non-T nucleotide (i.e. A, C or G) at the 3' end following the dT-stretch. By this means the Oligo(dT)-anchor primer is forced to bind to the (5') start site of the poly(A)-tail. Thus, the actual length of the poly(A)-tail has no influence on priming.

Alternatively, if a total population of RNA molecules shall be preamplified in an embodiment, where full length cDNA copies are not required, said 3' terminal part may comprise a completely randomized sequence of at least 5 nucleotides in length. In some cases it may be even desired to preamplify only the transcripts of a specific gene or a defined gene family. Then, said 3' terminal part may comprise a sequence complementary to a part of the consensus sequence of said gene family transcripts.

Single-stranded RNA is reverse transcribed during step b2) into single stranded DNA using a RNA-directed DNA polymerase. In this method, a polymerase such as the AMV-, MMLV-, HIV-reverse transcriptase or C. therm. Polymerase synthesizes the new DNA strand at a site(s) determined by the type of primer used: at the 3'-end of the poly(A)-mRNA when Oligo(dT) anchor-oligonucleotides are used as a primer, at non specific points along the template when using the Random-Hexamer-anchor-Primer, or at a primer-binding site for a sequence-specific anchor-primer. Furthermore it is possible to use Oligo(dT) or Oligo(dA) anchor-oligonucleotides as a primer in order to reverse transcribe single stranded RNAs that have been modified at their 3' end by a poly(A) or poly(U) tail by treatment with *E. Coli* Poly(A) Polymerase or poly(U) polymerase of *Schizosaccharomyces pombe*.

The terminal transferase treatment of step b3i) is applied to add a homopolymeric A-tail to the 3' end of the cDNA. However, in order to enable an efficient homopolymeric tailing specifically at the 3' end of the generated first strand cDNA, it is highly advantageous to perform the following two enzymatic treatments:

(i) It has been proven to be advantageous, if the non-hybridized and non-extended single-stranded DNA adaptor nucleic acid molecules added during step b1) are removed. As a result, the generation of reaction byproducts in the subsequent terminal transferase reaction is reduced. Thus a specific embodiment of the invention encompasses the step of removal of non-hybridized single-stranded DNA adaptor nucleic acid molecules added during step b1). In one embodiment, this can be achieved by means of a DNA exonuclease I treatment between steps b2) and b3i). This enzyme is a 3'to 5' exonuclease that is capable of single-stranded DNA which prevents an undesired elongation of said molecules during the terminal transferase reaction. Alternatively, such a removal can be achieved by means of chromatographic purification, for example by glass fibre adsorption mediated purification.

Furthermore, it has been proven to be advantageous, if dNTPs according to one aspect of the present invention are degraded prior to the terminal transferase reaction in step b3) in order to ensure a homopolymeric tailing in the subsequent terminal transferase reaction. Within the scope of the present invention, this may be achieved by an incubation with alkaline phosphatase between steps b2) and b3i).

preferably this incubation is performed after the treatment with DNA exonuclease I as disclosed above. After conventional heat inactivation of said alkaline phosphatase, dATP or another specific dNTP may be added in order to enable the generation of a homopolymeric extension product during the terminal transferase reaction.

Alternatively, non-hybridized and non-extended single-stranded DNA adaptor nucleic acid molecules as well as spare dNTPs can be removed by means of cDNA purification. Such a purification can be achieved by cDNA adsorption to silica beads or filter columns (Vogelstein, B. et al., Proc. Natl. Acad. Sci. U.S.A. 76 (1979) 615-619). Alternatively, cDNA purification can be achieved by its immobilization onto paramagnetic particles using specific buffer conditions like for example the Solid Phase Reversible Immobilization technology developed at the Whitehead Institute (De Angelis, M. M., Wang, D. G., and Hawkins, T. L., et al., Nucleic Acids Res. 23 (1995) 4742-47439).

As indicated above, the terminal transferase treatment is used to add a homopolymeric tail to the 3' end of the cDNA. Preferably, said identical dNTPs in step b3i) are dATPs such that a homopolymeric poly-A tail is generated. Since vertebrate coding sequences and 5' untranslated RNA regions tend to be biased toward G/C residues, the use of a poly (A)-tail decreases the likelihood of inappropriate truncation by the second Oligo dT-anchor primer. Additionally poly (A)-tail is used due to the weaker A/T binding than G/C binding, therefore longer stretches of A residues are required before the Oligo dT-anchor primer will bind to an internal site and truncate the amplification product.

First strand cDNA synthesis primarily results in the generation of a RNA/first strand cDNA hybrid. Experience has shown that the performances of DNA exonuclease I-, alkaline phosphatase- and terminal transferase reactions are not affected by the fact that the first strand cDNA molecule is still bound to its original template. However, second strand cDNA generation and in particular RT-PCR reactions are known to be less effective, in cases where the original template RNA has not been removed. Therefore, in a specific embodiment, the inventive method comprises the step of digesting the RNA by means of an RNAse H treatment to remove in the RNA within the RNA/DNA hybrid between steps b2) and b3i), but preferably after said incubation with the DNA exonuclease I and alkaline phosphatase. Alternatively, RNAse H may be added for digestion of the RNA template just during the terminal transferase reaction at step b3i).

The tailed cDNA molecules are then used for second strand cDNA synthesis. As a prerequisite, a second single stranded adaptor molecule is hybridized to said pool of single stranded cDNAs, said second single stranded adapter molecule comprising
- a 5' terminal part representing a primer binding site which is either identical or different to the 5' terminal part of said first single stranded adaptor molecule, and
- a 3' terminal part of homopolymeric nucleotide residues, which is complementary to said homopolymer overhang created in step b3i). In case homopolymeric A has been added during step b3i), said 3' terminal part is an oligo dT primer and preferably an oligodT anchor primer comprising at least one randomized 3' terminal residue and most preferably at least a randomized 3' terminal and a randomized 3' proxi-terminal residue.

In one embodiment, the 5' terminal part of said second single stranded adapter molecule is identical to the 5' terminal part of said first single stranded adaptor molecule. As a consequence, only 1 primer is required for the clonal amplification during step d).

In another embodiment, the 5' terminal part of said second single stranded adapter molecule is different to the 5' terminal part of said first single stranded adaptor molecule. As a consequence, clonal amplification in step d) will result in an directionally amplified library characterized in that all cDNA molecules are having the first specific adaptor sequence at the original 3' end and a second specific adaptor sequence at the 5' end.

Furthermore, it is also within the scope of the present invention, if the second adaptor sequence is introduced by means different from Terminal Transferase mediated tailing and subsequent primer hybridization.

For example, step b3), i.e. attaching a second single stranded adaptor molecule to said pool of single stranded cDNAs, may also be obtained by ligating a single stranded adaptor molecule to said pool of single stranded cDNAs. Said single stranded adaptor molecule is usually an oligonucleotide comprising a sequence which is complementary to a primer binding site as it is required for the subsequent amplification. Said primer may be either identical or different to the 5' terminal part of said first single stranded adaptor molecule.

Alternatively, said single stranded adaptor molecule are molecules comprising a
- a 5' terminal part representing a primer binding site which is either identical or different to the 5' terminal part of said first single stranded adaptor molecule, and
- a 3' terminal part of randomized nucleotide residues.

Advantageously, this embodiment does not require any intermediate enzymatic step such as homopolymeric tailing or ligation; however, the draw back is that due to the randomization of the second adaptor molecule sequence, first strand cDNAs are only amplified in the form of incomplete 3' ends.

Steps c) and d): Preparing a Water in Oil Emulsion and Clonally Amplifying Said Plurality of Different Nucleic Acid Molecules During step c), the aqueous sample containing the population of nucleic acid molecules with adaptor sequences attached to each side is mixed with an appropriate oil composition in order to generate a water in oil emulsion. The emulsion may be formed according to any suitable method known in the art. Any method for making an emulsion that does not abolish the activity of the Polymerase may be used. Respective methods are well known in the art.

Emulsions are heterogeneous systems of two immiscible liquid phases with one of the phases dispersed in the other as droplets of microscopic or colloidal size. Emulsions may be produced from any suitable combination of immiscible liquids. The emulsion used for the present invention has water (containing the biochemical components) as the phase present in the form of finely divided droplets (the disperse, internal or discontinuous phase) and a hydrophobic, immiscible liquid (an 'oil') as the matrix in which these droplets are suspended (the nondisperse, continuous or external phase). Such emulsions are termed 'water-in-oil' (W/O). This has the advantage that the entire aqueous phase containing the biochemical components is compartmentalised in discreet droplets (the internal phase). The external phase, being a hydrophobic oil, generally contains none of the biochemical components and hence is inert.

The emulsion may be stabilized by addition of one or more surface-active agents (surfactants). These surfactants are termed emulsifying agents and act at the water/oil interface to prevent (or at least delay) separation of the phases. Many oils and many emulsifiers can be used for the generation of water-in-oil emulsions; a recent compilation listed over 16,000 surfactants, many of which are used as emulsifying agents (Ash and Ash, 1993). Suitable oils include light white mineral oil and non-ionic surfactants (Schick, 1966) such as sorbitan monooleate (SPAN #8482; 80; ICI) and polyoxyethylenesorbitan monooleate (TWEEN #8482; 80; ICI).

The use of anionic surfactants may also be beneficial. Suitable surfactants include sodium cholate and sodium taurocholate. Particularly preferred is sodium deoxycholate, preferably at a concentration of 0.5% w/v, or below. Inclusion of such surfactants can in some cases increase the expression of the genetic elements and/or the activity of the gene products. Addition of some anionic surfactants to a non-emulsified reaction mixture completely abolishes translation. During emulsification, however, the surfactant is transferred from the aqueous phase into the interface and activity is restored. Addition of an anionic surfactant to the mixtures to be emulsified ensures that reactions proceed only after compartmentalisation.

Creation of an emulsion generally requires the application of mechanical energy to force the phases together. There are a variety of ways of doing this which utilise a variety of mechanical devices, including stirrers (such as magnetic stir-bars, propeller and turbine stirrers, paddle devices and whisks), homogenisers (including rotor-stator homogenisers, high-pressure valve homogenisers and jet homogenisers), colloid mills, ultrasound and 'membrane emulsification' devices.

Preferred methods in the context of the present invention include adjuvant methods, counter-flow methods, crosscurrent methods, rotating drum methods, and membrane methods. Furthermore, the size of the microcapsules may be adjusted by varying the flow rate and speed of the components. For example, in drop-wise addition, the size of the drops and the total time of delivery may be varied.

In one embodiment, amplification solution mixture is added dropwise into a spinning mixture of biocompatible oil (e.g., light mineral oil, Sigma) and allowed to emulsify. The oil used may be supplemented with one or more biocompatible emulsion stabilizers. These emulsion stabilizers may include ATLOX 4912, SPAN 80, AGRIMER AL22 (U.S. Pat. No. 7,575,865; EP 1 735 458) and other recognized and commercially available suitable stabilizers. Preferably, the droplets formed range in size from 5 micron to 500 microns, more preferably, from between about 50 to 300 microns, and most preferably, from 100 to 150 microns.

According to Williams et al. (Williams, R. et al., Nat. Methods 3 (2006) 545-550), an oil-surfactant mixture suitable for emPCR can be prepared by thoroughly mixing the following components in a 50-ml centrifuge tube at 25° C.:

| | |
|---|---|
| SPAN 20 | 4.5% final conc. |
| TWEEN 80 | 0.4% final conc. |
| TRITON X-100 | 0.05% final conc. |
| Mineral oil (Sigma) | ad 50 ml |

Subsequently, the aqueous phase to the oil-surfactant mixture in a dropwise manner over a period of 1.5 min with an additional continued stirring for 5 min. By this method, a water-in-oil emulsion can be generated containing approximately $10^8$-$10^9$ PCR-competent compartments per milliliter of emulsion. The tailed cDNA molecules are statistically distributed into an excess of aqueous droplets of a water-in-oil emulsion. Thereby the tailed cDNA molecules are segregated in the minute aqueous droplets of the emulsion so that individual, or at most a few, tailed cDNA molecules are amplified by PCR using primer complementary to the primer binding sites introduced at the 3' end and 5' end of the tailed cDNA. As disclosed above, the primer binding site at the 3' end of the cDNA has been added during cDNA tailing, whereas the primer binding site at the 5' end of the cDNA has been inserted during cDNA synthesis. This allows for a clonal amplification of the majority of originally generated single stranded cDNA molecules during subsequent step c).

More precisely, the conditions are chosen in such a way that the majority of water droplets comprises one or none member of said plurality of different nucleic acid molecules. It can be assumed that the distribution of numbers of tailed single stranded cDNA molecules follows a typical Poisson-type distribution. Thus a person skilled in the art will be capable of identifying conditions which fulfill the following two requirements:

First, the number of droplets needs to be large enough that more than 50% and preferably more than 80% of the droplets contain not more than one tailed cDNA molecule. This is the prerequisite for a clonal amplification during subsequent step d). Due to the principle of clonal amplification, i.e. individual amplification of each original single cDNA molecule, it is possible to obtain an unbiased population of amplified cDNA. In order to solve the problem underlying the invention. In other words, the representation frequency for each type of cDNA sequence that is found in the amplified population of cDNAs as a result of step d) shall correspond to the representation frequency for each type of cDNA sequence that is present in the originally provided plurality of different nucleic acid molecules.

Second, the number of aqueous droplets comprising no tailed cDNA template needs to be kept low enough in order to limit the requirement for emulsion and amplification reagents within steps c) and d) and thus render the method as effective as possible.

Step d) is executed in order to clonally amplify the tailed DNA within the aqueous droplets. Typically, such an amplification is achieved by means of PCR, which is known to be functional also within aqueous droplets within a water-in-oil emulsion (Margulies. M., et al., Nature Publ Group 437 (2005) 376-80; Nakano, M., et al., J. Biotechnol 102 (2003) 117-124). Also termed "emPCR" in the art, such an amplification method can be performed using standard thermocycling protocols.

The primers used for the emulsion PCR of step d) are oligonucleotides which are complimentary to the primer binding sites introduced by the first and second single stranded adapter molecules disclosed above. If the second adapter molecule contains a primer binding site identical to that of the first adapter molecule, only one primer is required for amplification. If the primer binding sites of both adapters are different, a pair of two different primers is necessary. In the latter case, a directional amplified cDNA is being generated.

The number of PCR cycles that is applied according to the invention ensuring that the double stranded cDNA will remain in the exponential phase of amplification can be optimized and predominantly depends, for example, on the initial concentration of sample DNA.

Afterwards, the emulsion is broken. Breaking the emulsion my be performed by appropriate filtration methods. Preferably, breaking of the emulsion may be achieved by treatment of said emulsion with isopropanol or detergent to recover the amplified cDNA library from the emulsion. Isopropanol treatment in combination with high speed centrifugation allows the recovery of nucleic acids from emulsion by quantitative precipitation. Detergent treatment using sodium dodecyl sulfate and TRITON X100 containing chaotropic buffers breaks the emulsion and allows the recovery of nucleic acids by adsorption to silica beads or filter columns.

According to Williams et al. (Williams, R. et al., Nat. Methods 3 (2006) 545-550), the emulsion can be broken by means of centrifugation at 13000 g for 5 min at 25° C. Dispose of the upper (oil) phase. Several extractions with an organic solvent such as water-saturated diethyl ether can further remove the remaining oil from the emulsion and cause it to break.

Read Out Methods

The inventive method is especially useful in order to analyze nucleic acids derived from only a small number of cells. In particular when said plurality of different nucleic acid molecules is derived from less than 100 cells, less than 10 cells and even only 1 cell. The obtained sample comprises amplified nucleic acid characterized in that all types of nucleic acid molecules originally present in the sample are represented in equal relative quantities as compared to their representation in the original sample, because the inventive method provides a solution for unbiased amplification. This provides a possibility of performing further quantitative analytical experiments with a high degree of accuracy. In particular, the present invention provides a solution for high accuracy gene expression analysis, when RNA and in particular mRNA is used as a starting material.

In a first embodiment, the clonally amplified plurality of different nucleic acid molecules may be subjected to qualitative or quantitative real time PCR reaction experiments using parameter specific amplification primers. Within real time PCR, sample analysis occurs concurrently with amplification in the same tube within the same instrument. The formation of PCR products is monitored in each cycle of the PCR. It is usually measured in thermocyclers which have additional devices for measuring fluorescence signals during the amplification reaction. DNA dyes or fluorescent probes can be added to the PCR mixture before amplification and used to analyze PCR products during amplification. This combined approach decreases sample handling, saves time, and greatly reduces the risk of product contamination for subsequent reactions, as there is no need to remove the samples from their closed containers for further analysis.

In one particular embodiment since the amount of double stranded amplification product usually exceeds the amount of nucleic acid originally present in the sample to be analyzed, double-stranded DNA specific dyes may be used, which upon excitation with an appropriate wavelength show enhanced fluorescence only if they are bound to double-stranded DNA. Preferably, only those dyes may be used which like SybrGreenI I, for example, do not affect the efficiency of the PCR reaction.

In another particular embodiment, fluorescently labeled Hybridization Probes which only emit fluorescence upon binding to its target nucleic acid can be used. For example, a single-stranded Hybridization Probe is labeled with two components. When the first component is excited with light of a suitable wavelength, the absorbed energy is transferred to the second component, the so-called quencher, according to the principle of fluorescence resonance energy transfer. During the annealing step of the PCR reaction, the hybridization probe binds to the target DNA and is degraded by the 5'-3' exonuclease activity of the Taq Polymerase during the subsequent elongation phase. As a result the excited fluorescent component and the quencher are spatially separated from one another and thus a fluorescence emission of the first component can be measured. TaqMan hydrolysis probe assays are disclosed in detail in U.S. Pat. Nos. 5,210,015, 5,538,848, and 5,487,972. TaqMan hybridization probes and reagent mixtures are disclosed in U.S. Pat. No. 5,804,375.

Alternatively, Molecular Beacon hybridization probes are labeled with a first component and with a quencher, the labels preferably being located at both ends of the probe. As a result of the secondary structure of the probe, both components are in spatial vicinity in solution. After hybridization to the target nucleic acids both components are separated from one another such that after excitation with light of a suitable wavelength the fluorescence emission of the first component can be measured (U.S. Pat. No. 5,118, 801).

Still alternatively, said real time PCR is monitored in real time by means of FRET hybridization probes. The FRET Hybridization Probe test format is useful for all kinds of homogenous hybridization assays including real time PCR (U.S. Pat. No. 6,174,670). It is characterized by two single-stranded hybridization probes which are used simultaneously and are complementary to adjacent sites of the same strand of the amplified target nucleic acid. Both probes are labeled with different fluorescent components. When excited with light of a suitable wavelength, a first component transfers the absorbed energy to the second component according to the principle of fluorescence resonance energy transfer such that a fluorescence emission of the second component can be measured when both hybridization probes bind to adjacent positions of the target molecule to be detected. Alternatively to monitoring the increase in fluorescence of the FRET acceptor component, it is also possible to monitor fluorescence decrease of the FRET donor component as a quantitative measurement of hybridization event.

In a second embodiment, the clonally amplified plurality of different nucleic acid molecules may be sequenced. Any kind of sequencing such as Sanger sequencing, or any method of high throughout sequencing may be performed. For example, sequencing may be performed on the 454 Genome Sequencer FLX System (Roche Applied Science). The system is capable of performing more than 1 million high-quality reads per run and read lengths of 400 bases, and thus ideally suited for de novo sequencing of whole genomes and transcriptomes of any size, metagenomic characterization of complex samples, resequencing studies and more. Using a series of standard molecular biology techniques, short adaptors (A and B)—specific for both the 3' and 5' ends—are added to each fragment that shall be sequenced. The adaptors are used for purification, amplification, and sequencing steps. Single-stranded fragments with A and B adaptors compose the sample library used for subsequent workflow steps. The single-stranded DNA library is immobilized onto specifically designed DNA Capture Beads. Each bead carries a unique single-stranded DNA library fragment. The bead-bound library is emulsified with amplification reagents in a water-in-oil mixture resulting in microreactors containing just one bead with one unique sample-library fragment. Each unique sample library fragment is amplified within its own microreactor. Amplification of the entire fragment collection is done in parallel; for each fragment, this results in a copy number of several million per bead. Subsequently, the emulsion PCR set up is broken while the amplified fragments remain bound to their specific beads. The fragments are then ready for loading onto a PicoTiterPlate device for sequencing. The diameter of the PicoTiterPlate wells allows for only one bead per well. After addition of sequencing enzymes, the fluidics subsystem of the Genome Sequencer FLX Instrument flows individual nucleotides in a fixed order across the hundreds of thousands of wells containing one bead each. Subsequently, a Pyrosequencing reaction is performed, and addition of one (or more) nucleotide(s) complementary to the template strand results in a chemiluminescent signal recorded by the CCD camera of the Genome Sequencer FLX.

For gene expression analysis, the whole population of amplified cDNA molecules is sequenced in massively parallel manner such that the relative abundances of different mRNA species can be compared. In this case, the present invention comprises the steps of a) providing a plurality of different mRNA molecules
b) attaching adaptor sequences to the 3' ends and 5' ends of said nucleic acid molecules, by means of
   b1) hybridizing a first single stranded adaptor nucleic acid molecule to said plurality of different nucleic acid molecules, said adapter molecule comprising
      a 5' terminal part representing a primer binding site, and
      a 3' terminal part which is an oligo dT sequence of at least 5 nucleotides in length,
   b2) performing a first strand cDNA synthesis to generate a pool of single stranded cDNAs
   b3i) performing a terminal transferase reaction in the presence identical dNTPs, which are preferably dATPs in order to create a homopolymer overhang,
   b3ii) hybridizing a second single stranded adaptor molecule to said pool of single stranded cDNAs, said second single stranded adapter molecule comprising
      a 5' terminal part representing a primer binding site which is either identical or different to the 5' terminal part of said first single stranded adaptor molecule, and
      a 3' terminal part of homopolymeric nucleotide residues, which is complementary to said homopolymer overhang created in step b3).
c) preparing a water in oil emulsion characterized in that the majority of water droplets comprises one or none member of said plurality of different nucleic acid molecules
d) clonally amplifying said plurality of different nucleic acid molecules.
e) sequencing said clonally amplified plurality of different nucleic acids.

If the a 5' terminal part representing a primer binding site which is actually different to the 5' terminal part of said first single stranded adaptor molecule, the method can be combined with the library of the 454 Genome Sequencer System. Thus the present invention is also directed to a method comprising the steps of a) providing a plurality of different mRNA molecules
b) attaching adaptor sequences to the 3' ends and 5' ends of said nucleic acid molecules, by means of
   b1) hybridizing a first single stranded adaptor nucleic acid molecule to said plurality of different nucleic acid molecules, said adapter molecule comprising
      a 5' terminal part representing a primer binding site, and
      a 3' terminal part which is an oligo dT sequence of at least 5 nucleotides in length,
   b2) performing a first strand cDNA synthesis to generate a pool of single stranded cDNAs
   b3i) performing a terminal transferase reaction in the presence identical dNTPs, which are preferably dATPs in order to create a homopolymer overhang,
   b3ii) hybridizing a second single stranded adaptor molecule to said pool of single stranded cDNAs, said second single stranded adapter molecule comprising
      a 5' terminal part representing a primer binding site which is either identical or different to the 5' terminal part of said first single stranded adaptor molecule, and
      a 3' terminal part of homopolymeric nucleotide residues, which is complementary to said homopolymer overhang created in step b3),
      wherein the 5'-terminus of said adapter molecule is attached to a bead
c) preparing a water in oil emulsion characterized in that the majority of water droplets comprises one or none member of said plurality of different nucleic acid molecules
d) clonally amplifying said plurality of different nucleic acid molecules within a water-in-oil emulsion, and
e) breaking said emulsion, and
f) sequencing said clonally amplified plurality of different nucleic acid molecules.

Finally, in order to monitor gene expression, the abundances of sequencing events counted for individual cDNAs sequences are compared to each other.

In a third embodiment, the clonally amplified plurality of different nucleic acid molecules may be hybridized onto DNA microarrays.

In order to detect the hybridization on a DNA microarray, it is required to label said clonally amplified plurality of different nucleic acid molecules with a fluorescent compound, which is later on detectable by a respective instrument such as a scanner. A preferred concept in the art for labeling a nucleic acid sample is random prime labeling. For this concept, a population of randomized primers with a length of 5-12 nucleotide monomers is first hybridized to the sample DNA. Then Klenow fragment DNA polymerase, which lacks 3' to 5' exonuclease activity is added in order to elongate said primers by means of and incorporating dNTPs. The label is being introduced by means of either using labeled primers or, alternatively, at least one type of labeled deoxynucleoside triphosphates. The label is preferably a fluorescent label and most preferred a Cyanine dye such as Cy3, Cy3.5, Cy5, or Cy5.5.

Thus, the present invention also encompasses a method for a) providing a plurality of different mRNA molecules b) attaching adaptor sequences to the 3' ends and 5' ends of said nucleic acid molecules, by means of
   b1) hybridizing a first single stranded adaptor nucleic acid molecule to said plurality of different nucleic acid molecules, said adapter molecule comprising
      a 5' terminal part representing a primer binding site, and
      a 3' terminal part which is an oligo dT sequence of at least 5 nucleotides in length,
   b2) performing a first strand cDNA synthesis to generate a pool of single stranded cDNAs
   b3i) performing a terminal transferase reaction in the presence identical dNTPs, which are preferably dATPs in order to create a homopolymer overhang,
   bii) hybridizing a second single stranded adaptor molecule to said pool of single stranded cDNAs, said second single stranded adapter molecule comprising a 5' terminal part representing a primer binding site which is either identical or different to the 5' terminal part of said first single stranded adaptor molecule, and a 3' terminal part of homopolymeric nucleotide residues, which is complementary to said homopolymer overhang created in step b3).

c) preparing a water in oil emulsion characterized in that the majority of water droplets comprises one or none member of said plurality of different nucleic acid molecules d) clonally amplifying said plurality of different nucleic acid molecules.

e) labeling said amplified plurality of nucleic acid molecules, preferably by means of random prime labeling, and f) hybridizing said labeled amplified plurality of nucleic acid molecules onto a DNA microarray.

A person skilled in the art will know how to design the probes that are required on an array which is used for monitoring gene expression. Alternatively, such gene expression arrays are commercially available (e.g. Roche Applied Science Cat. No: 05 543 789 001). Analysis of the fluorescent pattern emitted by the DNA microarray is then indicative for relative expression levels of individual RNAs.

Kits According to the Present Invention

In another aspect, the present invention is directed to kits useful for performing the inventive methods as disclosed above.

Such kits will comprise
a first single stranded adaptor nucleic acid molecule comprising
a 5' terminal part representing a primer binding site, and
a 3' terminal part which is either an oligo dT sequence of at least 5 nucleotides in length, or an essentially randomized sequence or a gene family specific sequence a second single stranded adaptor molecule to said pool of single stranded cDNAs, said second single stranded adapter molecule comprising
a 5' terminal part representing a primer binding site which is either identical or different to the 5' terminal part of said first single stranded adaptor molecule, and
a 3' terminal part of homopolymeric nucleotide residues an RNA dependent DNA polymerase comprising reverse transcriptase activity.

The RNA dependent DNA polymerase may be a reverse transcriptase such as TRANSCRIPTOR (Roche Applied Science Cat. No: 03 531 317 001), AMV reverse transcriptase (Roche Applied Science Cat. No: 11 495 062 001), M-MULV reverse Transcriptase (Roche Applied Science Cat. No: 11 062 603 001) or the Klenow fragment of DNA polymerase from Carboxydothermus hydrogenoformans (Roche Applied Science Cat. No: 12016346001).

Preferably the 3' terminal part of said first single stranded adaptor molecule comprised in such a kit comprises an oligo dT sequence of at least 5 nucleotides, or more preferably at least 15 but not more than 50 nucleotides in length.

Furthermore, the kit may comprise in addition one or several representatives of the following list of compounds, reagents and enzymes:

a Terminal Transferase (Roche Applied Science Cat. No: 03 333 566 001)

RNAse H (Roche Applied Science Cat. No: 10 786 349 001)

Alkaline Phosphatase (Roche Applied Science Cat. No: 11 097 075 001)

DNA exonuclease (New England Biolabs Cat. No: MO 293L)

an oil that can be used for performing a water in oil emulsion for emulsionPCR a thermostable DNA Polymerase which is capable of performing emPCR one or more species of Deoxynucleoside-triphosphates an amplification primer or a pair of amplification primers, which are oligonucleotides that are complimentary to the primer binding sites introduced by the first and second single stranded adapter molecules disclosed above.

If the second adapter molecule contains a primer binding site identical to that of the first adapter molecule, only one primer is required for amplification. If the primer binding sites of both adapters are different, a pair of two different primers is necessary.

EXAMPLE 1

Comparison of the Concordance in Gene Expression Between Unamplified cDNA Libraries and Pre-Amplified Libraries This comparison was performed using HeLa cells as source for total RNA. In particular comparison was performed on expression between unamplified cDNA libraries using unamplified cDNA libraries using the Roche TRANSCRIPTOR 1st stand cDNA synthesis kit (Roche Applied Science, #04379012001) as a calibrator sample, pre-amplified libraries using pre-existing Pre-Amplification Kits of the companies NuGen (Roche Applied Science, #05190894001), Rubicon/Sigma (# WTA1) and Clontech/Takara (#634925) according to the manufacturer's protocols, and a clonally pre-amplified library using the Clontech/Takara (#634925) Pre-amplification kit in a water in oil emulsion set up.

This Pre-Amplification in emulsion was performed on the basis of the Clontech/Takara SMARTer cDNA synthesis kit (#634925), with the following modification: total RNA was reverse transcribed using the SMARTer MMLV reverse transcriptase and a modified Oligo(dT) primer containing an universal anchor sequence (the 3' SMART CDS Primer IIA). When SMARTScribe RT reaches the 5' end of the mRNA, the enzyme's terminal transferase activity adds as few additional nucleotides to the 3' end of the cDNA. The SMARTer oligonucleotide IIA base-pairs with the non-template nucleotide stretch, creating an extended template. SMARTScribe RT then switches templates and continues replicating to the end of the oligonucleotide. The resulting single-stranded cDNA contained now two universal anchor sequences, one at is 5' end and one at its 3' end. These cDNAs were then distributed into an excess of aqueous droplets of a water in oil emulsion containing a PCR reaction mixture (polymerase, salts, buffer, dNTPs, primer) and mineral oil supplemented with one or more biocompatible emulsion stabilizers including ATLOX 4912, SPAN 80, AGRIMER AL22 and other recognized and commercially available suitable stabilizers. The amplification by PCR was based on a primer specific for the universal anchor sequences. After an optimal number of PCR cycles ensuring that the double stranded cDNA would remain in the exponential phase of amplification the emulsion was broken and the amplified cDNA library was recovered from the emulsion for additional comparative gene expression analysis by quantitative PCR.

The clonally amplified cDNA libraries were then used for relative gene expression analysis according to the comparative threshold cycle method (Livak, K. J. and Schmittgen, T. D., Methods 25 (2001)402-408; Schmittgen, T. D. and Livak, K. J., Nat. Protoc. 3 (2008) 1101-1108) using the Real Time Ready Human Reference Gene Panel (Roche Applied Science, #05 339 545 001) on a LightCycler 480 instrument (Roche Applied Science #05 015278 001).

In brief, relative gene expression was determined using HeLa cells as source for total RNA. cDNA synthesized from 5 ng total RNA using the TRANSCRIPTOR 1st stand cDNA synthesis kit (Roche Applied Science, #04379012001) was used as calibrator. On the basis of this calibrator Gene Expression was compared using 5 ng RNA each of the NuGen-Pre-Amplification-Kit, the Rubicon/Sigma WTA-Pre-Amplification-Kit, the Clontech/Takara SMARTer-Per-amplification-Kit and of a modified, emulsified SMARTer-Pre-Amplification-Kit.

The results of the qPCR expression analysis are summarized in the following table:

TABLE 1

Differences in relative gene expression monitoring using pre-amplification methods as compared to cDNA which is not pre-amplified.

| Gene | cDNA Syntesis kit | NuGen Preamp | Rubicon Preamp | Clontech Preamp | Clontech in emulsion Preamp |
|---|---|---|---|---|---|
| 18S | 1.00 | 26.53 | 31.99 | 0.02 | 0.49 |
| ACTB | 1.00 | 0.81 | 0.19 | 0.10 | 0.69 |
| ALAS | 1.00 | 2.03 | 1.88 | 5.74 | 0.86 |
| B2M | 1.00 | 0.44 | 1.61 | 6.54 | 3.79 |
| Beta-Globin | 1.00 | 0.00 | 0.03 | * | 1.02 |
| G6PDH | 1.00 | 2.43 | 0.60 | 0.00 | 0.53 |
| GAPDH | 1.00 | 1.30 | 0.04 | 9.58 | 5.63 |
| GUSB | 1.00 | 0.48 | 1.01 | 0.22 | 0.37 |
| HPRT1 | 1.00 | 0.15 | 0.09 | 1.61 | 2.55 |
| IPO8 | 1.00 | 1.68 | 3.46 | 0.47 | 0.21 |
| PBGD | 1.00 | 0.20 | 2.57 | 0.19 | 4.12 |
| PGK1 | 1.00 | 0.62 | 0.20 | 4.60 | 1.13 |
| PPIA | 1.00 | 6.63 | 4.82 | 3.58 | 1.77 |
| RPL13A | 1.00 | 1.80 | 0.52 | 2.64 | 2.85 |
| RPLP0 | 1.00 | 0.44 | 1.11 | 4.11 | 2.37 |
| SDHA | 1.00 | 0.20 | 0.25 | 0.09 | 0.97 |
| TBP | 1.00 | 45.87 | 8.28 | 0.66 | 1.02 |
| TFRC | 1.00 | 4.14 | 11.31 | 2.22 | 0.01 |
| YWHAZ | 1.00 | 11.47 | 6.82 | 2.48 | 2.22 |

* asterisks indicate a missing data point

As can be seen from the table the relative gene expression of target genes to the calibrator showed that using the Clontech preamplification kit in combination with a water in oil emulsion (see right column of table 1) resulted in least deviations from the values obtained for gene expression when analyzing the calibrator sample (cDNA synthesis kit only). Thus, the inventive method, i.e. performing clonal pre-amplification in a water in oil emulsion yields superior results over those methods that are available in the art.

EXAMPLE 2

Comparison of the Concordance in Gene Expression Between Unamplified cDNA Libraries and Pre-Amplified Libraries Prepared with an Additional Terminal Transferase Treatment This comparison was performed using HeLa cells as source for total RNA. In particular comparison was performed on expression between unamplified cDNA libraries using unamplified cDNA libraries using the Roche TRANSCRIPTOR 1st strand cDNA synthesis kit (Roche Applied Science, #04379012001) as a calibrator sample, and a clonally pre-amplified library on the basis of a modified 5'/3' RACE Kit (Roche Applied Science, #03353621001) in conjunction with a water in oil emulsion set up for pre-amplification.

The modifications were as follows: total RNA was reverse transcribed using the AMV based TRANSCRIPTOR reverse transcriptase and a modified Oligo(dT) primer containing an universal anchor sequence. After first strand cDNA synthesis unreacted primer was removed by glass fibre adsorption mediated purification of the cDNA (Roche Applied Science, #11732668001).

Subsequently a terminal transferase treatment was used to add a homopolymeric A-tail to the 3' end of the cDNA. Tailed cDNA molecules were then used for second strand cDNA synthesis using a DNA-polymerase and a second oligo dT-anchor primer.

In addition, tailed cDNA molecules were statistically distributed into an excess of aqueous droplets of a water in oil emulsion containing a PCR reaction mixture (polymerase, salts, buffer, dNTPs, primer) and mineral oil supplemented with one or more biocompatible emulsion stabilizers including ATLOX 4912, SPAN 80, AGRIMER AL22 and other recognized and commercially available suitable stabilizers (see also patents (U.S. Pat. No. 7,575,865; EP 1 735 458). Thereby the tailed cDNA molecules were segregated in the minute aqueous droplets of the emulsion so that individual, or at most a few, tailed cDNA molecules are amplified by PCR using a primer specific to the anchor-primer. After an optimal number of PCR cycles ensuring that the double stranded cDNA would remain in the exponential phase of amplification the emulsion was broken and the amplified cDNA library was then recovered from the emulsion.

The clonally amplified cDNA libraries were then used for relative gene expression analysis as disclosed in example 1. The results of the qPCR expression analysis are summarized in the following table:

TABLE 2

Differences in relative gene expression monitoring using pre-amplification methods as compared to cDNA which is not pre-amplified.

| Gene | Unamplified cDNA library (500 ng RNA) | Emulsion PCR Pre-amplified cDNA library (50 ng RNA) |
|---|---|---|
| 18S | 1.00 | 0.01 |
| ACTB | 1.00 | 0.67 |
| ALAS | 1.00 | 1.44 |
| B2M | 1.00 | 0.61 |
| Beta-Globin | 1.00 | * |
| G6PDH | 1.00 | 0.91 |

TABLE 2-continued

Differences in relative gene expression monitoring
using pre-amplification methods as compared
to cDNA which is not pre-amplified.

| Gene | Unamplified cDNA library (500 ng RNA) | Emulsion PCR Pre-amplified cDNA library (50 ng RNA) |
|---|---|---|
| GAPDH | 1.00 | 10.90 |
| GUSB | 1.00 | 0.02 |
| HPRT1 | 1.00 | 0.81 |
| IPO8 | 1.00 | 0.24 |
| PBGD | 1.00 | 6.01 |
| PGK1 | 1.00 | 5.64 |
| PPIA | 1.00 | 0.95 |
| RPL13A | 1.00 | 0.53 |
| RPLP0 | 1.00 | 2.32 |
| SDHA | 1.00 | 2.08 |
| TBP | 1.00 | 0.00 |
| TFRC | 1.00 | 0.10 |
| YWHAZ | 1.00 | 6.76 |

* asterisks indicate a missing data point

As can be seen from the table the relative gene expression of target genes to the calibrator showed that 18 out of 19 genes could be successfully pre-amplified by the water-in-oil emulsion based protocol described above. The concordance with the calibrator samples was high for medium to low expressed target genes (absolute Cp≥25) whereas the expression level of the more abundant genes in the sample were frequently overestimated. This indicates that the inventive method, i.e. performing clonal pre-amplification in a water-in-oil emulsion, provides superior results either for the analysis of target transcripts with an initially low RNA concentration in the sample or for the pre-amplification of RNA from samples where minute amounts of total RNA are present (e.g. analysis of few cells derived from a fine needle biopsy or analysis at the single cell level).

What is claimed is:

1. A method of generating an unbiased population of amplified cDNA comprising the steps of:
    (a) providing a plurality of different single-stranded RNA molecules, the plurality comprising different single-stranded RNA molecules present at different representation frequencies in the plurality,
    (b)-(b1) hybridizing a first adaptor molecule to the 3' ends of RNA molecules of said plurality,
        the first adaptor molecule comprising a 5' terminal part comprising a primer binding site, and
        a 3' terminal part comprising an oligo (dT) sequence at least 5 nucleotides in length, a randomized sequence at least 5 nucleotides in length, or a specific sequence for a gene or gene family,
    (b2) performing a first strand cDNA synthesis in the presence of an RNA-dependent DNA polymerase and a dNTP mixture to generate a pool of single-stranded cDNA molecules,
    (b3) attaching a second adaptor molecule to cDNA molecules of said pool,
    (c) preparing a water-in-oil emulsion by statistically distributing the cDNA molecules obtained in step (b3) into an excess of aqueous droplets of a water-in-oil emulsion so that a majority of water droplets comprise one or zero cDNA molecules; and
    (d) clonally amplifying the cDNA molecules within the emulsion using polymerase chain reaction to produce an amplified population comprising different cDNA molecules present at representation frequencies that are about equal to the representation frequency of the different single-stranded RNA molecules present in the plurality.

2. The method according to claim 1, wherein the second adaptor attaching step (b3) comprises
    (b3i) performing a terminal transferase reaction in the presence of one specific dNTP to create a homopolymer overhang, and
    (b3ii) hybridizing a second adaptor molecule to cDNA molecules of said pool, the second adaptor molecule comprising: a 5' terminal part comprising a primer binding site which is either identical to or different from the 5' terminal part of the first adaptor molecule, and
        a 3' terminal part of homopolymeric nucleotide residues, which is complementary to the homopolymer overhang.

3. The method according to claim 2, wherein
    the single-stranded RNA molecules of said plurality are mRNA molecules,
    the 3' terminal part of the first adaptor molecule comprises an oligo (dT) sequence at least 5 nucleotides in length, and
    the one specific dNTP is dATP.

4. The method according to claim 2, wherein the 3' terminal part of the first adaptor molecule comprises a randomized sequence at least 5 nucleotides in length or a specific sequence for a gene or gene family.

5. The method according to claim 2, wherein the second adaptor molecule comprises a 5' terminal part comprising a primer binding site which is identical to the 5' terminal part of the first adaptor molecule.

6. The method according to claim 3, further comprising the step of degrading the dNTP mixture with alkaline phosphatase before the step of performing a terminal transferase reaction.

7. The method according to claim 3, further comprising the step of removing RNA molecules from the pool of single-stranded cDNA molecules with RNAse H.

8. The method according to claim 3, further comprising the step of removing the first adaptor molecule from the pool of single-stranded cDNA molecules with a 3'-5' exonuclease.

9. The method of either claim 7 or 8, wherein the removing step occurs when the second adaptor molecule is not present in the pool of single-stranded cDNA molecules.

10. The method of claim 8, wherein the 3'-5' exonuclease is DNA exonuclease I.

11. The method according to claim 1, further comprising the steps of
    (e) breaking up the emulsion of clonally amplified molecules; and
    (f) sequencing the clonally amplified nucleic acid molecules.

12. The method according to claim 1, further comprising the steps of
    (e) breaking up the emulsion of clonally amplified molecules; and
    (f) performing a real-time PCR reaction on the clonally amplified nucleic acid molecules.

13. The method according to claim 1, further comprising the steps of
    (e) breaking up the emulsion of clonally amplified molecules; and
    (f) performing a DNA microarray analysis on the clonally amplified nucleic acid molecules.

14. The method according to claim 1, wherein the plurality of single-stranded RNA molecules is derived from less than 100 cells.

15. The method according to claim 1, wherein the plurality of single-stranded RNA molecules is derived from less than 10 cells.

16. The method according to claim 1, wherein the plurality of single-stranded RNA molecules is derived from 1 cell.

17. The method according to claim 1, wherein the 3' terminal part of the first adaptor molecule comprises a randomized sequence at least 5 nucleotides in length or a specific sequence for a gene or gene family.

18. The method according to claim 1, wherein the second adaptor molecule comprises a 5' terminal part comprising a primer binding site which is identical to the 5' terminal part of the first adaptor molecule.

* * * * *